United States Patent [19]
Garlick

[11] Patent Number: 5,179,455
[45] Date of Patent: Jan. 12, 1993

[54] ULTRASONIC HOLOGRAPHIC IMAGING APPARATUS HAVING AN IMPROVED OPTICAL RECONSTRUCTION SYSTEM

[75] Inventor: George F. Garlick, Kennewick, Wash.

[73] Assignee: Advanced Imaging Systems, Richland, Wash.

[21] Appl. No.: 796,716

[22] Filed: Nov. 22, 1991

[51] Int. Cl.[5] .......................... G01N 29/04; G03H 3/00
[52] U.S. Cl. ........................................ 359/9; 73/603; 73/605; 359/559; 359/901; 367/8; 367/10
[58] Field of Search .................... 359/3, 9, 901, 559, 359/564; 73/603, 605; 367/8, 10

[56] References Cited

U.S. PATENT DOCUMENTS

| | | |
|---|---|---|
| 3,561,257 | 2/1971 | Brenden .............................. 359/901 |
| 3,564,905 | 2/1971 | Brenden et al. . |
| 3,585,847 | 6/1971 | Brenden . |
| 3,715,482 | 2/1973 | Haines et al. ........................... 359/9 |
| 3,721,312 | 3/1973 | St. John .................................. 359/9 |
| 3,765,403 | 10/1973 | Brenden . |
| 3,829,827 | 8/1974 | Ernvein ............................... 359/901 |
| 3,879,989 | 4/1975 | Brenden ............................. 359/901 |
| 5,084,776 | 1/1992 | Watson .................................. 359/3 |

Primary Examiner—Martin Lerner
Attorney, Agent, or Firm—Wells, St. John, Roberts, Gregory & Matkin

[57] ABSTRACT

A preferred embodiment of the optical reconstruction assembly 50 in which the assembly 50 includes an assembly housing 52 that is a unitary unit for supporting a spatial filter 72 and a light source 74 in a single plane at the optical length "L" from a collimating lens 86. A liquid container 88 is mounted to the assembly housing 52 containing the holographic liquid 90. The light source 74 and the spatial filter 72 are spaced a fixed distance "A" which is less than the optical diameter "D" of the collimating lens 86.

29 Claims, 4 Drawing Sheets

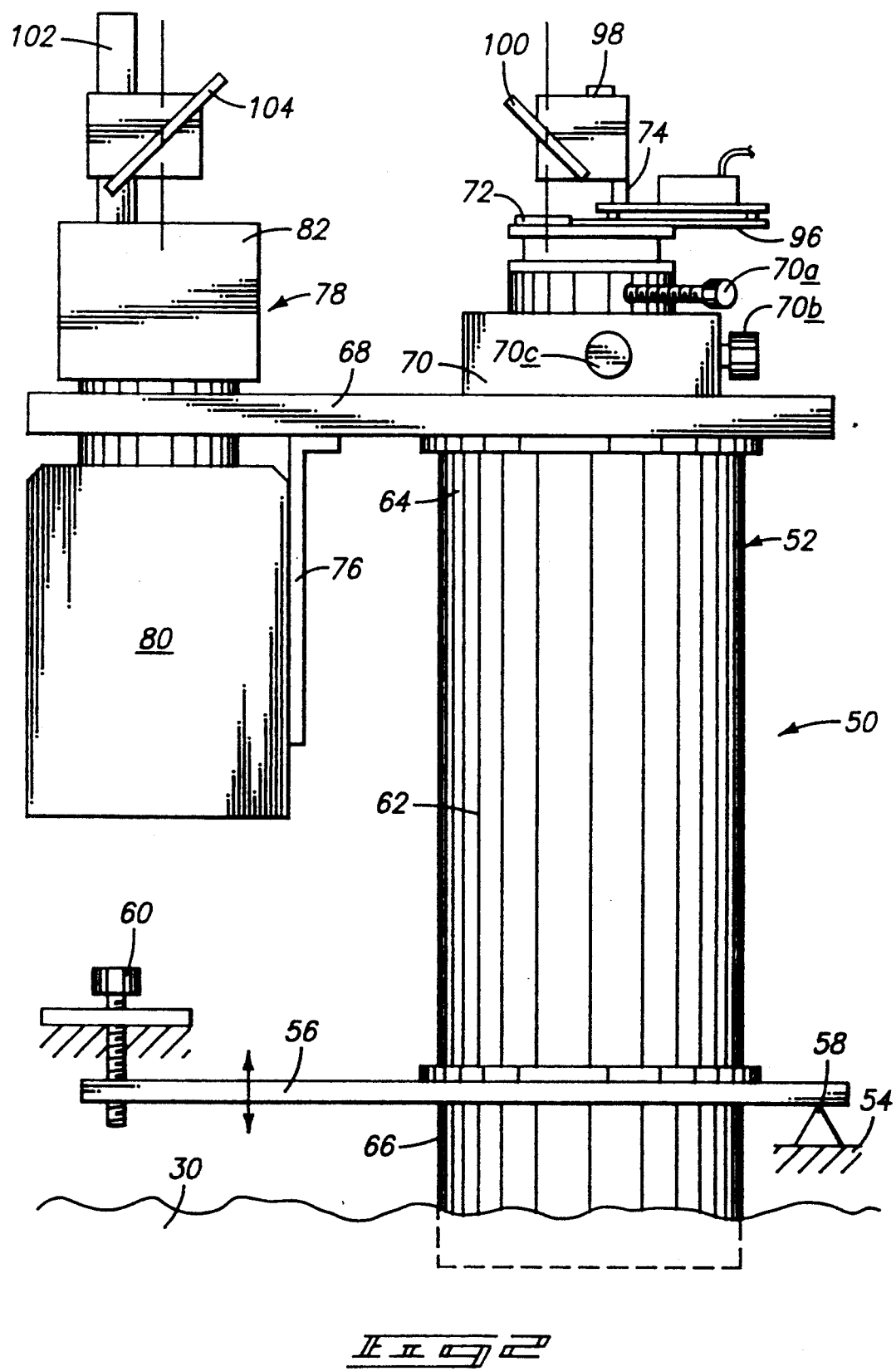

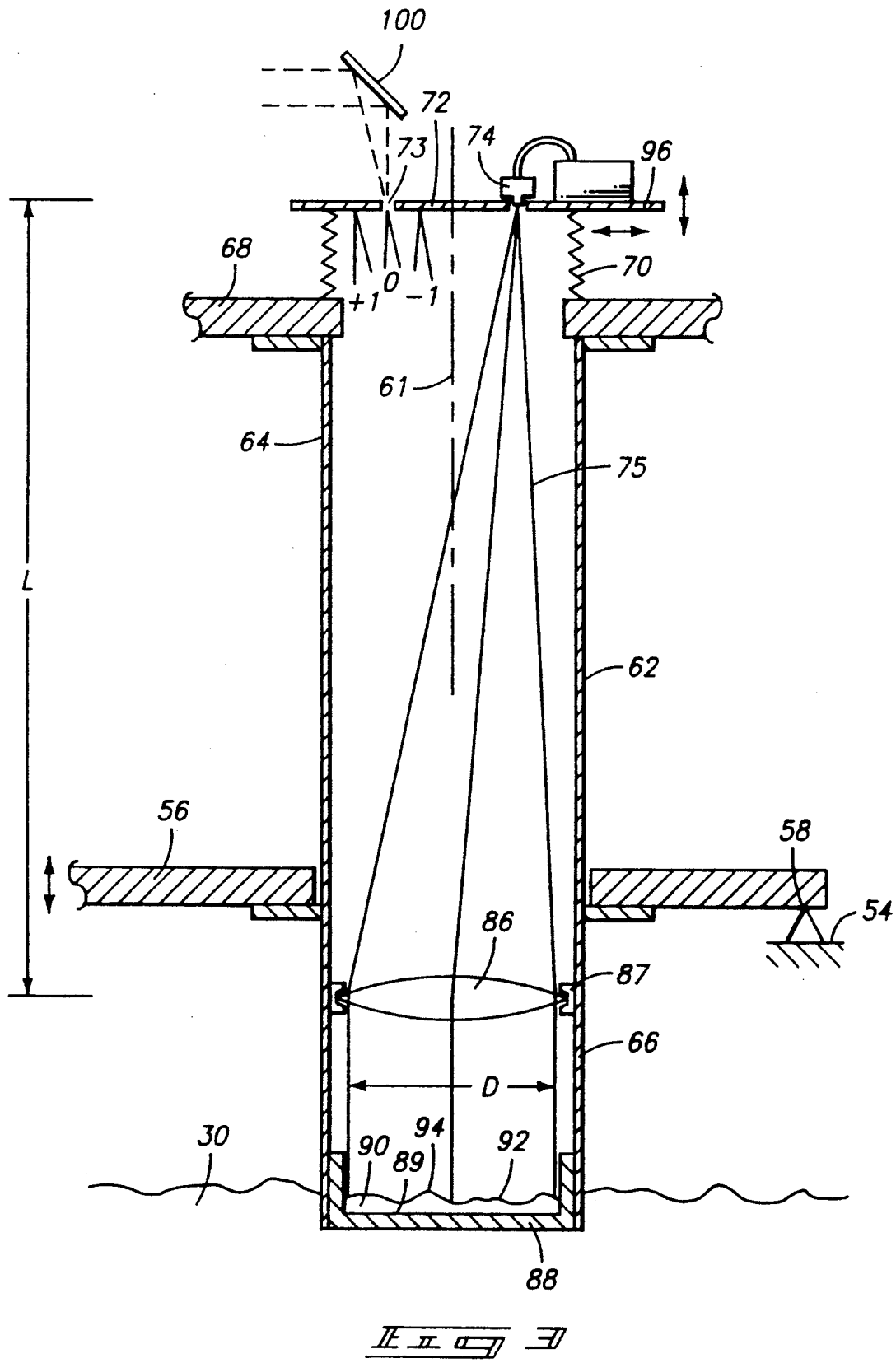

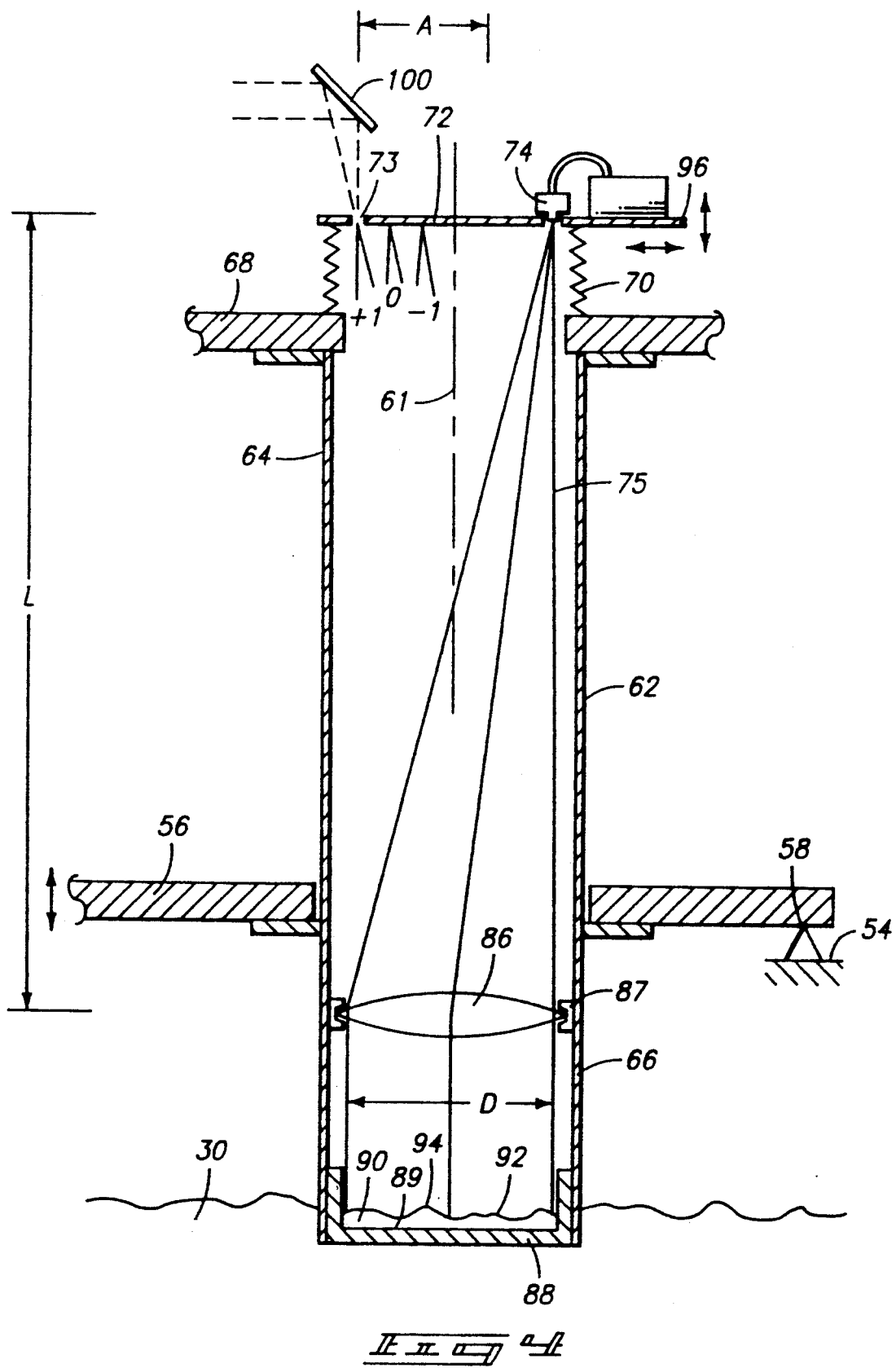

ULTRASONIC HOLOGRAPHIC IMAGING APPARATUS HAVING AN IMPROVED OPTICAL RECONSTRUCTION SYSTEM

TECHNICAL FIELD

This invention relates to an ultrasonic holographic imaging apparatus for producing an ultrasonic hologram of an object and more particularly to such apparatus having systems for optically reconstructing a visual image of the object from the ultrasonic hologram.

BACKGROUND OF THE INVENTION

Although commercial application of ultrasonic holography as been accurately pursued by many persons in the scientific and industrial communities for many years, only limited results have been obtained even though it was once thought that ultrasonic holography held great promise. It was felt that the application of ultrasonic holography was particularly applicable to the fields of nondestructive testing of materials and medical diagnostics of soft tissues that are relatively transparent to ultrasonic radiation. One of the principal problems that has been encountered and not effectively resolved is the difficulty of obtaining quality and consistent images.

Solutions to this problem have been elusive, in part because of the difficulty in identifying the many causes that contribute to the problem. It is believed that one of the major problems has been the difficulty in devising or constructing accurate an optical reconstruction system that is compatible with an ultrasonic hologram imaging apparatus to provide consistent, high quality images.

FIG. 1 shows a typical prior art "real time" ultrasonic holographic imaging apparatus generally designated with the numeral 10. The apparatus 10 is intended to ultrasonically inspect the interior of an object 12 such as the soft tissue of a human limb. The ultrasonic holographic imaging apparatus 10 generally has a hologram generating system 14 for generating an ultrasonic hologram. The apparatus 10 also includes a prior art hologram viewing subsystem (optical-subsystem) 16 for optically viewing the interior of the object 12 from a first order diffraction from the formed ultrasonic hologram.

The system 14 includes an object ultrasonic transducer 18 for generating plane waves through a coupling medium 20 contained in a deformable membrane 22. The deformable membrane 22 intimately contacts the object 12 on one side and a deformable membrane 24 contacts the object on the other side to provide ultrasonic coupling with minimum energy loss or wave distortion. The deformable membrane 24 forms part of the side wall of a container 28 that contains a liquid coupling medium 30.

One of the components is a prior art horizontal ultrasonic imaging lens system 32 for viewing a large field and focusing at a desired object focal plane 34. The ultrasonic imaging lens system 32 focuses the ultrasonic energy onto a hologram detector surface 36. The ultrasonic imaging lens system 32 includes a large diameter object lens 38 that is moveable with respect to a large diameter lens 40 for adjusting the desired focal plane 34 in the object 12. The ultrasonic imaging lens system 32 includes a mirror 41 for reflecting the ultrasonic energy vertically approximately 90° and onto the hologram detection surface 36 to form the hologram.

An ultrasonic reference transducer 42 directs coherent ultrasonic plane waves through the liquid medium 30 at an off-axis angle to the hologram detector surface 36 to form the hologram. Preferably, the hologram detection surface 36 is a liquid surface of a liquid/gas interface that is supported in an isolating dish or minitank 44.

The prior art hologram viewing system 16 includes an optical lens 45 to achieve an effective point source of a horizontal coherent light beam from a laser (not shown). The focused coherent light beam is reflected from a mirror 46, 90 degrees, through a collimating optical lens 47 and then onto the hologram detector surface 36 to illuminate the hologram and generate diffracted optical beams. The diffracted coherent light radiation containing holographic information is directed back through the collimating lens 47 and separated into precisely defined different order diffracted beams in the focal plane of the collimating lens 47. A filter 48 is used to block all but first order diffracted beams from a viewing lens 49 to enable a human eye, a photographic film or a video camera to record, in "real time", an image of the object taken at the object focal plane. As previously mentioned, although such an apparatus is operable, it has been difficult to obtain quality and consistent images.

One of the principal objects and advantages of this invention is to provide an improved ultrasonic holographic imaging apparatus that has a unique optical reconstruction system that overcomes many of the disadvantages of the previous optical reconstruction systems to provide images of high quality.

These and other objects and advantages of this invention will become apparent upon reading the following detailed description of a preferred embodiment.

BRIEF DESCRIPTION OF THE DRAWINGS

Preferred embodiments of the invention are described below with reference to the accompanying drawings, which are briefly described below.

FIG. 2 is a vertical side elevational view of an optical reconstruction system of the preferred embodiment of the invention;

FIG. 3 is a vertical cross sectional view of a portion of the system illustrated in FIG. 2 illustrating the generation of a coherent hologram illuminating beam and the generation and the spatial filtering of diffracted beams from the ultrasonic hologram with the light source and spatial filter in a calibration position;

FIG. 4 is a vertical cross-sectional view similar to FIG. 3 except showing the light source and the spatial filter being in an operational position.

DETAILED DESCRIPTION OF THE PREFERRED EMBODIMENTS

Figure 1:
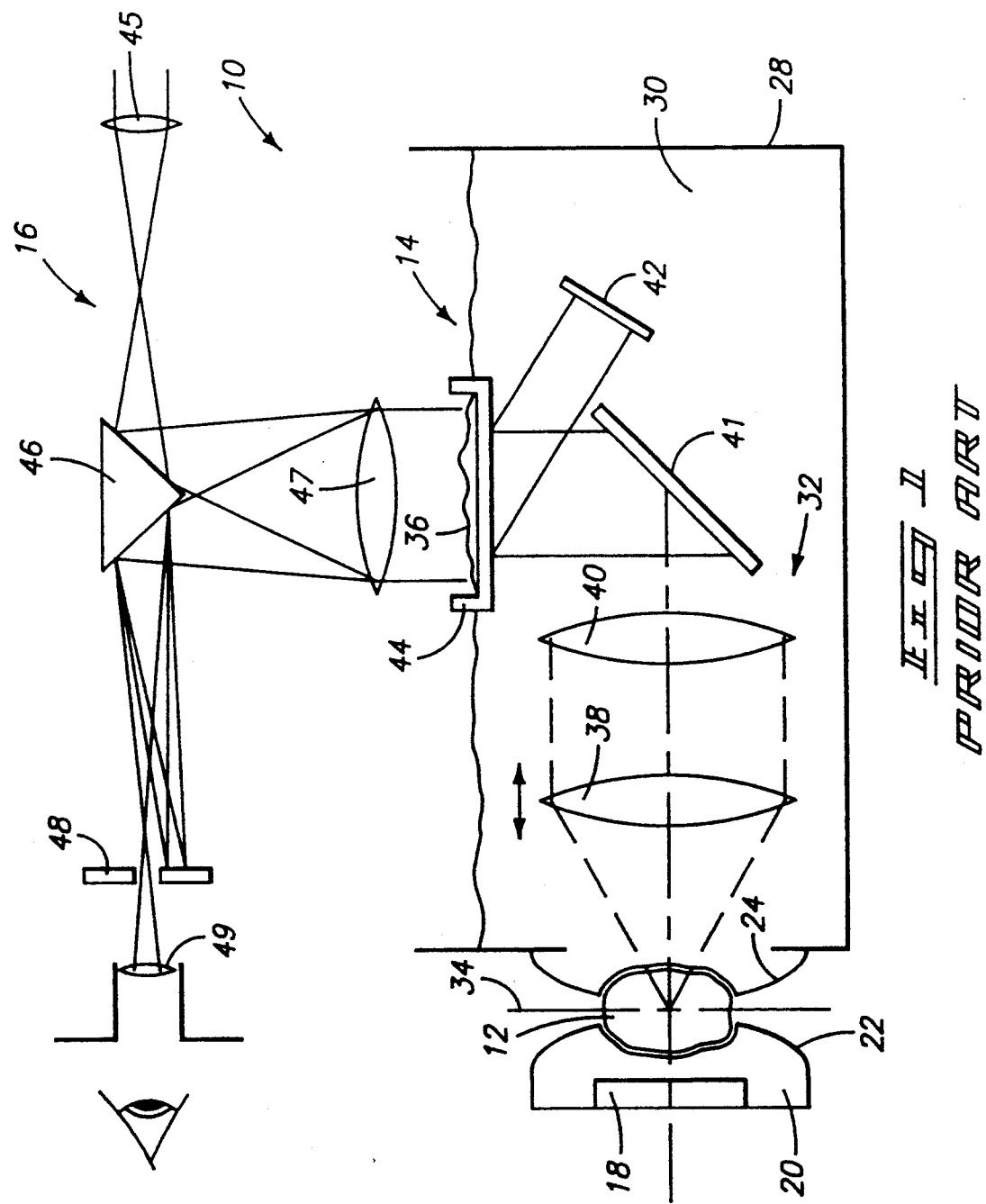
FIG. 1 is a schematic side elevational view of a prior art ultrasonic holographic system illustrating a typical optical reconstruction system.

This disclosure of the invention is submitted in furtherance of the constitutional purposes of the U.S. Patent Laws "to promote the progress of science and useful arts" (Article 1, Section 8).

Referring to FIG. 2, there is illustrated a preferred embodiment of the ultrasonic holographic imaging apparatus having an optical reconstruction assembly, generally designated with the numeral 50. Assembly 50 includes an assembly housing 52 that is a unitary housing that is movable as a single assembly even though the housing may be composed of various parts that are connected together in a fixed relationship. The housing 52 is supported on a support frame 54 of the ultrasonic holographic imaging apparatus. The support frame 54 has a pivot plate 56 supporting the assembly housing 52 for pivoting the housing 52 about a horizontal axis 58 to accurately calibrate and align the optical reconstruction assembly relative to the holographic generation system 14 of the apparatus. The assembly 50 includes a calibration or adjusting means 60 for accurately pivoting the pivot plate 56 about the horizontal axis 58 to vertically align an optical axis (FIGS. 3 and 4) with the holographic generation system 14.

The assembly housing 52 includes a beam enclosure 62 that is in the form of a cylinder that extends from an upper portion 64 that extends above the pivot plate 56 and a lower portion 66 that extends downwardly from the horizontal axis 58 terminating an elevation below the liquid level of the liquid coupling means 30.

An optic plate 68 is mounted at the upper portion 64, having an adjustable fixture 70 affixed thereon for supporting a spatial filter 72 and a light source 74. Fixture 70 is preferably a commercially available optical translation fixture commonly used in optical systems. Light source 74 is preferably a small diameter point source laser diode which is connected to complementary electronic elements 75. The laser diode preferably generates coherent light in the infrared spectrum. The spatial filter 72 includes a transparent element 73 that preferably is a small aperture permitting the transmission of a single diffracted light beam therethrough.

The assembly housing 52 includes a bracket 76 (FIG. 2) that is mounted on the optic plate 68 for supporting a visual observation means 78 that is preferably a video camera 80. Video camera 80 is preferably mounted in a generally vertical orientation having a focusing lens 82 for adjusting the focus of the video camera to visually inspect a first order diffracted holographic beam containing an image of the insonified object.

An important element of the optical reconstruction assembly 50 is a collimating lens 86 (FIGS. 3 and 4) that is mounted in the beam enclosure 62 adjacent the lower portion 66. The collimating lens is mounted within the beam enclosure 52 by a mounting bracket 87 that is a part of the assembly housing 62. The collimating lens has a preselected optical diameter "D" and an optical focus length "L".

The optical reconstruction assembly 50 additionally includes a liquid container 88 that is affixed to the lower portion 66 of the beam enclosure 62. The container 88 may be referred to as a mini-tank and contains the holographic liquid 90 that has a liquid surface 92 on which the hologram 94 is formed. As illustrated in FIGS. 3 and 4, the lower portion 66 of the assembly housing 52 extends downwardly so that at least a portion of the container 88 projects into the liquid 30 to provide a liquid coupling between the liquid 30 and the holographic liquid 90. The liquid 90 may be water or another suitable low viscous liquid. Preferably the container 88 has a flat bottom surface 88 so that the optical axis 61 of the collimating lens 86 is perpendicular to the bottom surface 89 of the container 88. Consequently, when the optical axis 61 is vertical, the optical axis then is perpendicular to the liquid surface 92.

The light source 74 is mounted on a support plate 96 of the adjustment fixture 70 for X, Y, Z movement. The adjustment fixture 70 is adjusted by a vertical adjustment knob 70a to position the light source 74 at the focal length "L" from the collimating lens 86 as illustrated in FIGS. 3 and 4. The light source 74 is positioned at a distance from the optical axis that is less than one half of the optical diameter "D".

The light source 74 generates a coherent light beam 75 that is directed downward through the collimating lens 86 illuminating the liquid surface 92 and generating a series of refracted beams from the hologram 94 that contain image information of the object 12.

Spatial filter 72 is additionally mounted on the support plate 96 to be positioned by the adjustment fixture 70 at the focal length "L" from the collimating lens 86. The light source 74 and the spatial filter 72 are positioned in substantially the same plane normal to the axis 61. The spatial filter 72 has a transparent element 73 in the form of an aperture that permits the transmission of one of the diffracted beams. As illustrated in FIGS. 3 and 4, the zero order, +1 order and −1 order diffracted beams are focused at the spatial filter 72. The purpose of the spatial filter 72 is to block most of the diffracted beams and to transmit one or two of the diffracted beams through the filter to the visual observation means 78.

Preferably the transparent element 73 of the spatial filter 72 is always positioned within a distance from the optical axis 61 that is less than one-half of the diameter "D" of the collimating lens 86. Preferably the distance between the transparent element 73 and the light source 74 is a fixed distance "A" that is less than the diameter "D" of the collimating lens 86.

Positioning the light source 74 as close to the optical axis 61 as possible provides for maximum uniform intensity illumination of the hologram 94. The adjustment fixture 70 has adjustment knobs 70b and 70c for aligning the support plate 96 and the light source 74 and the spatial filter 72 in lateral alignment with the optical axis 61. Once alignment is obtained, then the spatial filter 72, light source 74, collimating lens 86 and the liquid surface 92 are all in alignment with the optical axis 61.

FIG. 3 illustrates the optical reconstruction assembly 50 being in a calibration position in which the adjustment fixture 70 is adjusted through turning the knob 70b to move both the light source 74 and the spatial filter 72 in unison so that the transparent element 73 receives and transmits the zero order diffracted beam. Concurrently the calibration adjustment means 60 is manipulated to adjust the optical axis 61 with respect to the liquid surface 92 to place the vertical axis vertical and perpendicular to the liquid surface so that the distance between the light source 74 and the optical axis 61 is equal to the distance between the optical axis 61 and the transparent element 73. When this occurs, the zero order diffracted beam is focused at the element 73.

After optical calibration of the assembly 50 has been obtained, the knobs 70b or 70c, or both, are rotated to move the support plate 96 laterally with respect to the optical axis 61 to move the light source 74 and the spatial filter 72 in unison until the transparent element 73 transmits one of the first order diffracted beams (+1 or −1). Optically, the spatial filter 72 may include two apertures that are appropriately spaced so that both the +1 and −1 zero diffracted order beams are transmitted through the spatial filter 72 during the operational phase of the assembly. It should be noted that very little movement is required of light source 74 and the spatial filter 72 to obtain operational alignment positioning since a one half degree movement in the optical beam 75 will cause a one degree movement in the diffracted beams.

At the operational position, as illustrated in FIG. 4, the first order refracted beam containing image information is passed through the spatial filter 72 and is reflected from a mirror 100 that is mounted on an upright 98 of the assembly housing 52. The mirror 100 directs the transmitted first order diffracted beam approximately 90° to a second mirror 104 that is mounted on an upright 102 to direct the first order diffracted beam downwardly to the focusing lens 82 of the video camera 80.

It should be appreciated that once the light source and spatial filter 72 are aligned with the optical axis 61 and the optical axis 61 is perpendicular to the planar bottom surface 89 of the container 88 and the video camera focusing lens 82 and the mirrors 100 and 104 are properly positioned, then the entire assembly housing 52 operates as a single unitary unit for pivotal movement about the horizontal axis 58. Consequently the assembly housing 52 when assembled into the ultrasonic holographic imaging apparatus merely needs to be placed in position and a single adjustment of calibration means 70 and adjustment means 60 to vertically align the optical axis 61 with respect to the liquid surface 92 to obtain complete optical alignment of the system. Then the only adjustment that needs to be made is to operate the adjustment fixture 70 to move the light source 74 and the spatial filter 72 a slight distance to position transparent element 73 at a first order diffracted beam so that the video camera 80 observes an image of the object.

Although the beam enclosure 62 is in the form of a cylinder, the system is operable if the beam enclosure 62 is L-shaped and has a mirror for reflecting the light beam from the light source 74 and the diffracted beams approximately 90° to a vertical axis. In this invention, it is understood that the optical axis 61 is the effective optical axis of the collimating lens.

In compliance with the statute, the invention has been described in language more or less specific as to methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. An ultrasonic holographic imaging apparatus for forming an ultrasonic hologram of an object and for generating a visual image of the object from the ultrasonic hologram, comprising:
   a) an ultrasonic holographic detection surface composed of a liquid surface of a selected liquid;
   b) an ultrasonic transducer means for (1) directing an object beam of ultrasound through the object and onto the holographic detection surface, and (2) directing a reference beam onto the holographic detention surface interfering with the object beam to form an ultrasonic hologram on the detection surface;
   c) an optical reconstruction assembly for forming a visual image of the object from the ultrasonic hologram, comprising:
      1) an optical collimating lens having an optical axis;
      2) a source of coherent light aligned relative to the optical axis for generating a coherent light beam and directing the light beam through the collimating lens illuminating the hologram on the liquid surface and generating a plurality of diffracted beams from the liquid surface;
      3) a spatial filter aligned relative to the optical axis projecting into paths of the diffracted beams in which the filter has a transparent element for transmitting at least one of the diffracted beams defining an unfiltered diffracted beam containing an optical image of the object through the spatial filter;
      4) observation means projecting into the path of the unfiltered diffracted beam for viewing the optical image; and
      5) an assembly calibrating means operatively connected to the collimating lens, the coherent light source and the spatial filter for moving the collimating lens, the coherent light source and the spatial filter in unison to align the optical axis perpendicular to the liquid surface.

2. The ultrasonic holographic imaging apparatus as defined in claim 1 wherein the collimating lens has a preselected diameter and wherein the light source is positioned adjacent the optical axis at a distance that is less than one-half of the collimating lens diameter.

3. The ultrasonic holographic imaging apparatus as defined in claim 1 wherein the collimating lens has a preselected diameter and wherein the transparent element of the spatial filter is positioned adjacent the optical axis at a distance that is less than one-half of the collimating lens diameter.

4. The ultrasonic holographic imaging apparatus as defined in claim 1 wherein the collimating lens has a preselected diameter and a preselected focal length and wherein the light source is positioned along the optical axis at a distance substantially equal to the focal length of the collimating lens.

5. The ultrasonic holographic imaging apparatus as defined in claim 1 wherein the collimating lens has a preselected diameter and a preselected focal length and wherein the spatial filter is positioned along the optical axis at a distance substantially equal to the focal length of the collimating lens.

6. The ultrasonic holographic imaging apparatus as defined in claim 1 wherein the collimating lens has a preselected diameter and a preselected focal length and wherein both the light source and the spatial filter are positioned along the optical axis at distances substantially equal to the focal length of the collimating lens.

7. The ultrasonic holographic imaging apparatus as defined in claim 6 wherein the light source and the spatial filter are mounted in substantially the same plane at the focal length distance from the collimating lens.

8. The ultrasonic holographic imaging apparatus as defined in claim 1 wherein the collimating lens has a prescribed diameter and wherein the light source and the transparent element of the spatial filter are spaced relative to each other a distance less than the diameter of the collimating lens.

9. The ultrasonic holographic imaging apparatus as defined in claim 1 wherein the collimating lens, the light source and the spatial filter are supported on a common housing that is movably mounted and wherein the assembly calibrating means is operatively connected to the common housing for moving the housing to align the optical axis of the collimating lens perpendicular to the hologram liquid surface.

10. The ultrasonic holographic imaging apparatus as defined in claim 1 wherein the observation means is also supported on the common housing.

11. The ultrasonic holographic imaging apparatus as defined in claim 10 wherein the observation means is a video camera.

12. The ultrasonic holographic imaging apparatus as defined in claim 1 wherein the optical reconstruction system includes a container receiving the hologram liquid that is operatively connected to the assembly calibrating means.

13. The ultrasonic holographic imaging apparatus as defined in claim 1 wherein both the light source and the spatial filter are mounted on a fixture element that is laterally movable relative to the optical axis to enable the light source and the spatial filter to be moved in unison relative to the optical axis.

14. The ultrasonic holographic imaging apparatus as defined in claim 13 wherein the collimating lens has a preselected diameter and wherein the light source and the spatial filter are mounted on the fixture element at a spaced distance of less than the prescribed diameter.

15. The ultrasonic holographic imaging apparatus as defined in claim 14 wherein the light source and the spatial filter are mounted on the fixture element in substantially the same plane that is normal to the optical axis.

16. The ultrasonic holographic imaging apparatus as defined in claim 1 wherein the assembly calibration means is mounted for pivotal movement about a horizontal axis spaced from the optical axis to pivotally move the collimating lens, light source and spatial filter in unison about the horizontal axis to align the optical axis perpendicular to the liquid surface.

17. The ultrasonic holographic imaging apparatus as defined in claim 1 wherein the transparent element of the spatial filter comprises an aperture to permit a diffracted beam to pass through the filter.

18. The ultrasonic holographic imaging apparatus as defined in claim 1 wherein both the spatial filter and the light source are mounted in substantially the same plane that is normal to the optical axis in which the spatial filter and the light source are mounted for lateral movement in unison relative to each other to adjust the relative spacing from the optical axis.

19. The ultrasonic holographic imaging apparatus as defined in claim 18 wherein both the light source and the spatial filter are mounted on a laterally movable fixture element for moving both the light source and the spatial filter between a calibration position in which the transparent element of the spatial filter and the light source are equally spaced from the optical axis and an operational position in which the transparent element of the spatial filter and the light source are unequally spaced from the optical axis with the transparent element positioned to pass a first order diffracted beam.

20. In an ultasonic holographic imaging apparatus for forming an ultrasonic hologram of an object,
    an optical reconstruction assembly for forming a visual image of the object from the ultrasonic hologram, comprising:
    a) an unitary assembly housing;
    b) an optical collimating lens mounted to the unitary assembly housing, in which the lens has a preselected lens diameter and a preselected focal length relative to an optical axis;
    c) a source of coherent light mounted to the unitary assembly housing for generating a coherent light beam and directing the light beam through the collimating lens to illuminate the hologram and generate a plurality of diffracted beams from the hologram, including a zero order diffracted beam and a first order diffracted beam;
    d) a spatial filter mounted to the unitary assembly housing for projecting into the path of the plurality of diffracted beams in which the spatial filter has a transparent element for transmitting at least one of the diffracted beams while blocking others; and
    e) an observation means for receiving one of the transmitted beams to visually view the object and
    f) wherein the unitary assembly housing operatively interconnects the optical collimating lens, the source of coherent light and the spacial filter to enable the optical collimating lens, the source of coherent light and the spacial filter to be moved in unison while maintaining the source of coherent light and the spacial filter in fixed relationship to the optical collimating lens.

21. In the ultrasonic holographic imaging apparatus as defined in claim 20 wherein the housing includes an adjustment fixture centered along the optical axis for movable supporting both the light source and spatial filter in substantially the same plane normal to the optical axis and for adjustably moving the light source and spatial filter laterally relative to the optical axis to position the spatial filter in an operational position for transmitting the first order diffracted beam through the transparent element while blocking transmission of the zero order diffracted beam.

22. In the ultrasonic holographic imaging apparatus as defined in claim 21 wherein the light source and spatial filter are supported on the adjustment fixture at a distance less than the diameter of the collimating lens and at a distance from the collimating lens substantially equal to the focal length of the collimating lens.

23. In the ultrasonic holographic imaging apparatus as defined in claim 21 wherein the light source and the spatial filter are movable supported for movement in unison between a calibration position in which the light source and the transparent element of the spatial filter are equally spaced from the optical axis and the operation position in which the light source and transparent element are unevenly spaced from the optical axis.

24. In the ultrasonic holographic imaging apparatus as defined in claim 20 wherein the light source and spatial filter are spaced a distance less than the diameter of the collimating lens.

25. In the ultrasonic holographic imaging apparatus as defined in claim 20 wherein the unitary assembly housing includes an enclosure extending between the collimating lens and the spatial filter and light source for enclosing the beams.

26. In the ultrasonic holographic imaging apparatus as defined in claim 20 wherein the optical reconstruction assembly includes a liquid container mounted on the unitary assembly housing centered with respect to the optical axis, in which the container has a liquid with a liquid surface on which the ultrasonic hologram is formed.

27. The ultrasonic holographic imaging apparatus as defined in claim 26 wherein the unitary assembly housing is mounted for pivotal movement about a horizontal axis; and a calibration means operatively connected to the assembly housing for pivoting the assembly until the optical axis is perpendicular to the surface of the liquid.

28. The ultrasonic holographic imaging apparatus as defined in claim 20 wherein the source of coherent light is substantially a point source.

29. The ultrasonic holographic imaging apparatus as defined in claim 28 wherein the point source is a laser diode.

* * * * *